United States Patent
Sato et al.

(10) Patent No.: US 7,342,995 B2
(45) Date of Patent: Mar. 11, 2008

(54) APPARATUS FOR ESTIMATING SPECIFIC POLYMER CRYSTAL

(75) Inventors: Takahisa Sato, Akishima (JP); Akihito Yamano, Akishima (JP); Shoichi Yasukawa, Akishima (JP); Hiroki Yoshida, Akishima (JP); Kensaku Hamada, Himeji (JP)

(73) Assignees: Rigaku Corporation, Tokyo (JP); RIKEN, Saitama (JP)

( * ) Notice: Subject to any disclaimer, the term of this patent is extended or adjusted under 35 U.S.C. 154(b) by 0 days.

(21) Appl. No.: 10/568,740

(22) PCT Filed: Aug. 18, 2004

(86) PCT No.: PCT/JP2004/012142

§ 371 (c)(1),
(2), (4) Date: Feb. 17, 2006

(87) PCT Pub. No.: WO2005/017513

PCT Pub. Date: Feb. 24, 2005

(65) Prior Publication Data

US 2006/0266954 A1   Nov. 30, 2006

(30) Foreign Application Priority Data

Aug. 18, 2003 (JP) ............................ 2003-207771

(51) Int. Cl.
*G01N 23/223* (2006.01)
*G21K 4/00* (2006.01)

(52) U.S. Cl. .............................. 378/46; 378/43; 378/47

(58) Field of Classification Search .................. 378/42, 378/44–51, 70–73, 79
See application file for complete search history.

(56) References Cited

U.S. PATENT DOCUMENTS

| | | | | |
|---|---|---|---|---|
| 4,964,150 A | * | 10/1990 | Van Der AA et al. | 378/197 |
| 5,214,288 A | * | 5/1993 | Oka et al. | 250/373 |
| 5,353,236 A | * | 10/1994 | Subbiah | 700/266 |
| 7,144,457 B1 | * | 12/2006 | McRee et al. | 117/2 |
| 2002/0067800 A1 | * | 6/2002 | Newman et al. | 378/73 |

FOREIGN PATENT DOCUMENTS

| | | |
|---|---|---|
| JP | 4-216441 | 8/1992 |
| JP | 7-35687 | 2/1995 |
| JP | 2003-194741 | 7/2003 |
| JP | 2004-20397 | 1/2004 |
| JP | 2004-526949 | 9/2004 |
| WO | WO-02/057763 | 7/2002 |

* cited by examiner

*Primary Examiner*—Edward J. Glick
*Assistant Examiner*—Irakli Kiknadze
(74) *Attorney, Agent, or Firm*—Jordan and Hamburg LLP

(57) ABSTRACT

A specific macromolecule crystal evaluating device according to the present invention is equipped with a sample detecting stage for detecting a protein crystal in a sample container, an X-ray measuring stage that is spaced from the sample detecting stage and carries out X-ray diffraction measurement of the protein crystal, a feeding unit for feeding the sample container from the sample detecting stage to the X-ray measuring stage, and a central processing unit for recognizing the position of the protein crystal on the basis of the information achieved in the sample detecting stage and controlling the feeding unit on the basis of the position information to position the protein crystal to a sample disposing portion of the X-ray measuring stage.

7 Claims, 12 Drawing Sheets

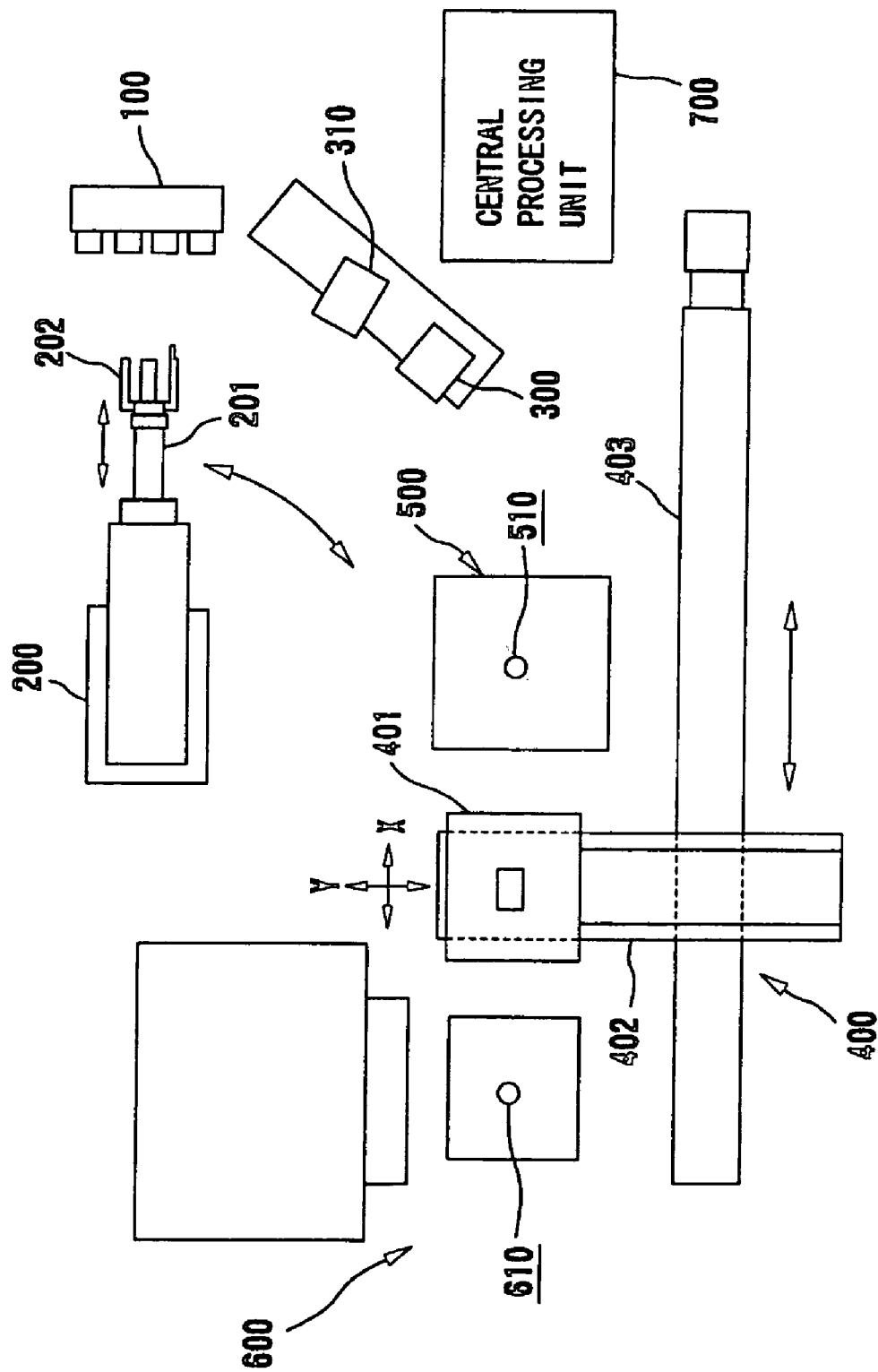

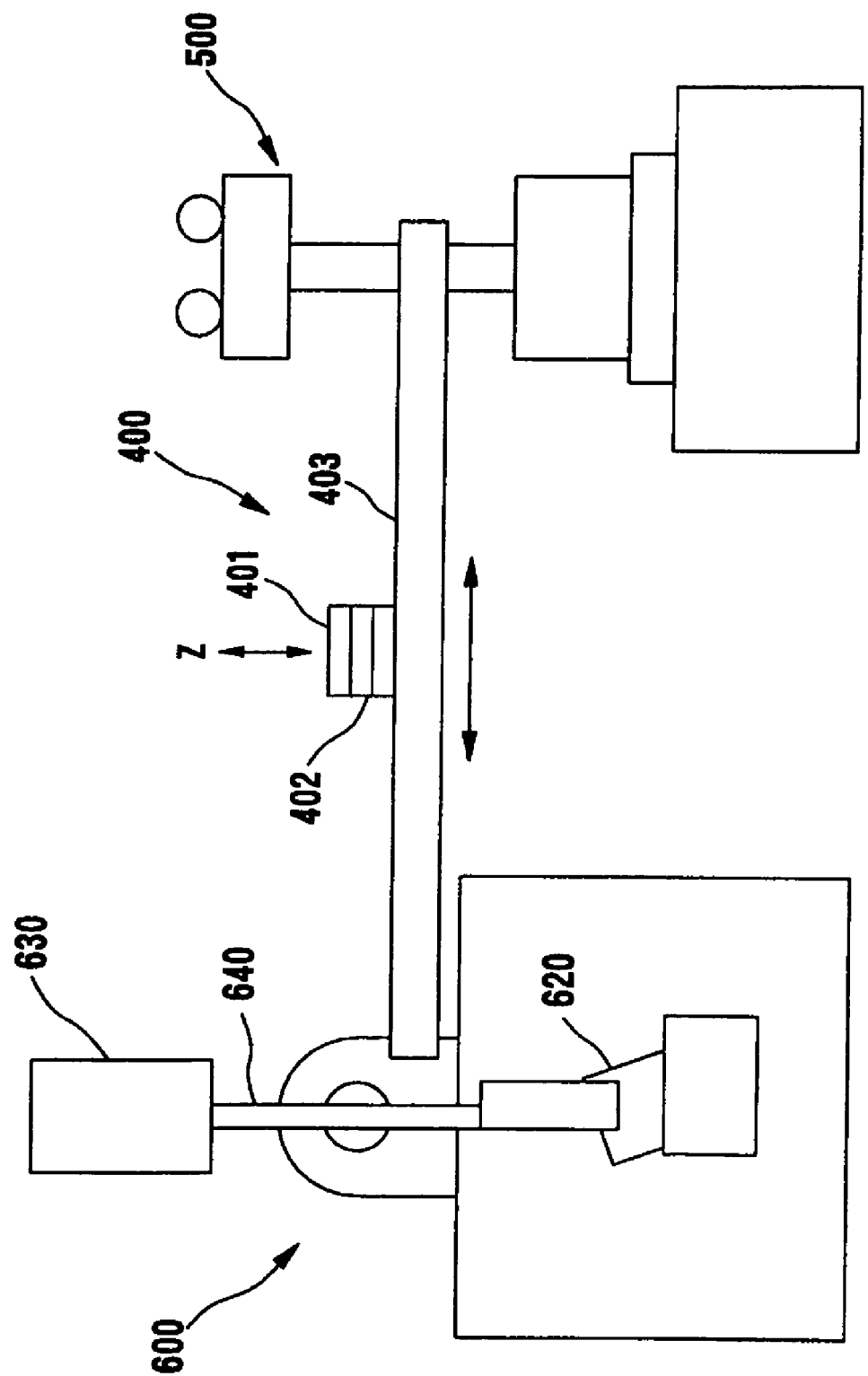

Fig.8

| 3 | 2 | 1 |
|---|---|---|
| 4 | NOTED PIXEL (x, y) | 8 |
| 5 | 6 | 7 |

APPARATUS FOR ESTIMATING SPECIFIC POLYMER CRYSTAL

BACKGROUND OF THE INVENTION

The present invention relates to a specific polymer crystal estimating apparatus, namely a specific macromolecule crystal evaluator, for evaluating specific macromolecule crystal by utilizing an X-ray diffraction phenomenon, and particularly an apparatus suitable to evaluate biological polymer crystal such as protein crystal or the like.

Worldwide attention has been paid to the structural analysis of protein crystals in connection with the development in the genome plan since a double helix structure of DNA was discovered. A method using NMR (Nuclear Magnetic Resonance apparatus) a method using an electron microscope, a method using the X-ray diffraction phenomenon, etc. have been developed for the structure analysis of protein crystals, and particularly the X-ray crystal structure analysis using the X-ray diffraction phenomenon has been rapidly advanced in connection with the developments of a two-dimensional X-ray detector such as an imaging plate or the like, analyzing software for two-dimensional data, etc.

The protein crystal structural analysis using the X-ray diffraction phenomenon has been hitherto carried out as follows. First, protein is crystallized in solution to achieve protein crystals, and a protein crystal thus achieved is placed in a glass tubule called as a capillary. Under this state, the structural analysis is carried out while the capillary is set in an X-ray diffraction apparatus.

In order to conduct the X-ray structural analysis on protein crystal, it is required to carry out a work of accurately positioning the protein crystal as a target to an X-ray irradiation position. Therefore, it has been hitherto general that a microscope for detecting a protein crystal is affixed to an X-ray diffraction apparatus, and an operator manually positions the protein crystal through visual observation by using the microscope. The positioning operation based on the visual observation and the manual labor as described above is cumbersome and it takes much time. In addition, since the positioning operation in the X-ray diffraction apparatus has been hitherto required to be carried out every time one measuring operation is finished, and thus it has been impossible to quickly evaluate many protein crystals.

For example, it is said that the number of kinds of proteins constituting the human body extends to 50,000 to 100,000 kinds, and it has been an urgent issue in the recent structural biology that the structures of many protein crystals are clarified in a short time.

The present invention has been implemented in view of the foregoing situation, and has an object to automate the structural analysis of specific macromolecule crystals by using the X-ray diffraction phenomenon to thereby speed up the processing thereof.

SUMMARY OF THE INVENTION

In order to attain the above object, according to the present invention, an apparatus for using a sample container through which X-ray, ultraviolet light and visible light are transmissible and evaluating specific macromolecule crystals existing in the sample container is characterized by comprising:

A sample detecting stage for detecting the specific macromolecule crystal in the sample container;

an X-ray measuring stage that is disposed so as to be spaced from the sample detecting stage and carries out an X-ray diffraction measurement of the specific macromolecule crystal;

feeding means for feeding the sample container from the sample detecting stage to the X-ray measuring stage; and control means for recognizing the position of the specific macromolecule crystal on the basis of information achieved in the sample detecting stage and controlling the feeding means on the basis of the position information to position the specific macromolecule crystal to a sample disposing portion of the X-ray measuring stage.

As described above, the specific macromolecule crystal in the sample container is detected by the sample detecting stage, and the feeding means is controlled on the basis of the information achieved there to position the specific macromolecule crystal to the sample disposing portion of the X-ray measuring stage. Therefore, the work from the detection of the specific macromolecule crystal to the positioning to the sample disposing portion can be automated, and the evaluating processing can be speeded up.

Particularly when a protein crystal is evaluated, a crystallization plate on which many recess portions for generating protein crystals are formed is used as the sample container, and a protein crystal is generated in each recess portion of the crystallization plate. Each protein crystal is detected by the sample detecting stage, and then the crystallization plate is fed to the X-ray measuring stage. The protein crystals in the respective recess portions are successively subjected to the X-ray diffraction measurement while positioned to the sample disposing portion, whereby many protein crystals can be sequentially evaluated and the working time can be greatly reduced.

Here, the sample detecting stage may comprise specific macromolecule crystal detecting means for irradiating ultraviolet light to the sample container and detecting a fluorescent image emitted from the sample in the sample container, and crystal detecting means for detecting the outline of the sample from a visible light image of the sample existing in the sample container.

Furthermore, the control means judges as a specific macromolecule crystal the sample for which the fluorescent image is detected by the specific macromolecule detecting means and the outline showing the crystal is detected by the crystal detecting means, and recognizes the position of the specific macromolecule crystal.

Many polymer crystals, particularly biological polymers generate fluorescence when ultraviolet light is irradiated to them. In this specification, a polymer crystal having a characteristic that it generates fluorescence when ultraviolet light is irradiated to the polymer crystal concerned will be referred to as "specific macromolecule crystal". For example, protein crystals are contained in the specific macromolecule crystal.

According to the present invention, taking notice of the characteristic of the specific macromolecule crystal as described above, ultraviolet light is irradiated to a sample container, and a fluorescent image emitted from a sample in the sample container concerned is detected, thereby detecting the specific macromolecule in the sample container.

However, there is a case where it is not identifiable by only the fluorescent image whether the thus-detected specific macromolecule forms a crystal. For example, when aggregation of the specific macromolecule exists in the sample container, the aggregation concerned generates fluorescence, and thus the fluorescent image caused by the crystal and the fluorescent image caused by the aggregation are detected with being mixed with each other.

Therefore, according to the present invention, the outline of the sample is detected on the basis of a visible light image of the sample existing in the sample container, and discriminates the crystal from the other materials on the basis of the outline thereof. Accordingly, the "crystal" of the "specific macromolecule" is identified by cooperating the above result with the detection result of the fluorescent image, and the position of the specific macromolecule crystal concerned is recognized.

Furthermore, the X-ray measuring stage comprises:

X-ray irradiating means for irradiating X-ray from the upper side or lower side to the specific macromolecule crystal in the sample container disposed in the sample disposing portion;

X-ray detecting means that is disposed so as to confront the X-ray irradiating means through the sample container, and detects diffracted X-ray from the specific macromolecule crystal transmitted through the sample container;

a rotary arm for supporting the X-ray irradiating means and the X-ray detecting means; and a rotationally driving mechanism for rotating the rotary arm with respect to the substantially horizontal shaft center by any angle.

According to the above construction, the integrated intensity of the diffracted X-ray from the specific macromolecule crystal can be determined without rotating the sample container. The integrated intensity of the diffracted X-ray is determined by detecting the intensity of the diffracted X-ray when X-ray is irradiated to the crystal from various angles while varying the X-ray irradiation angle to the crystal, and integrating the intensity data thus achieved. It has been hitherto general that the integrated intensity of the diffracted X-ray is determined by rotating a capillary in which a crystal sample is encapsulated.

In order to analyze the structure of the specific macromolecule crystal such as protein crystal or the like, it is required to determine the integrated intensity of X-ray diffracted from the crystal. That is, reflected X-ray from a crystal which may cause diffraction is spherically distributed in the reciprocal space (diffraction space). Accordingly, the peak intensities of the diffracted X-ray (diffraction spots) detected at positions fixed with respect to the crystal are achieved by observing only one cross section of the reflected X-ray distributed spherically as described, and the number of them is merely equal to one several hundredths to one several thousandths of the number of peak intensities required for the structural analysis of a crystal (that is, determination of a molecular structure).

According to the present invention, by rotating the X-ray irradiating means and the X-ray detecting means relatively to a sample holder, the peak intensities (diffraction spots) can be detected from plural cross sections with respect to the reflected X-ray from the crystal which is spherically distributed, and the integrated intensity of the thus-detected peak intensities can be determined. As a result, the analysis/evaluation of the crystal structure having high reliability can be implemented on the basis of the integrated intensity of the diffracted X-ray thus detected.

Particularly when a crystallization plate is used as a sample container, solution is filled in recess portions of the crystallization plate, and specific macromolecule crystals such as protein crystals or the like exist in this solution with being floated. Accordingly, when the crystallization plate is rotated, the solution gets out of the crystallization plate or crystals in the solution move. Therefore, it is impossible to rotate the crystallization plate. However, according to the apparatus of the present invention, the integrated intensity of the diffracted X-ray can be determined without rotating the crystallization plate.

Furthermore, the feeding means comprises a sample table on which a sample container is mounted, an XYZ table for mounting the sample table thereon and moving the sample table in X and Y directions orthogonal to each other on the horizontal plane and in the height direction, and a slider for feeding the XYZ table from the sample detecting stage to the X-ray measuring stage (claim 4).

By controlling the driving of the XYZ table and the slider, the specific macromolecule crystal existing in the sample container can be automatically positioned to the sample disposing portion provided to the X-ray measuring stage, and thus the workability can be remarkably enhanced.

BRIEF DESCRIPTION OF THE DRAWINGS

FIG. 1 is a schematic plan view showing the overall construction of a specific macromolecule crystal evaluating apparatus according to an embodiment of the present invention.

FIG. 2 is a schematic front view.

FIG. 8 is a diagram showing edge detecting processing of step S11 shown in FIG. 7.

DETAILED DESCRIPTION OF THE INVENTION

Figure 3A:
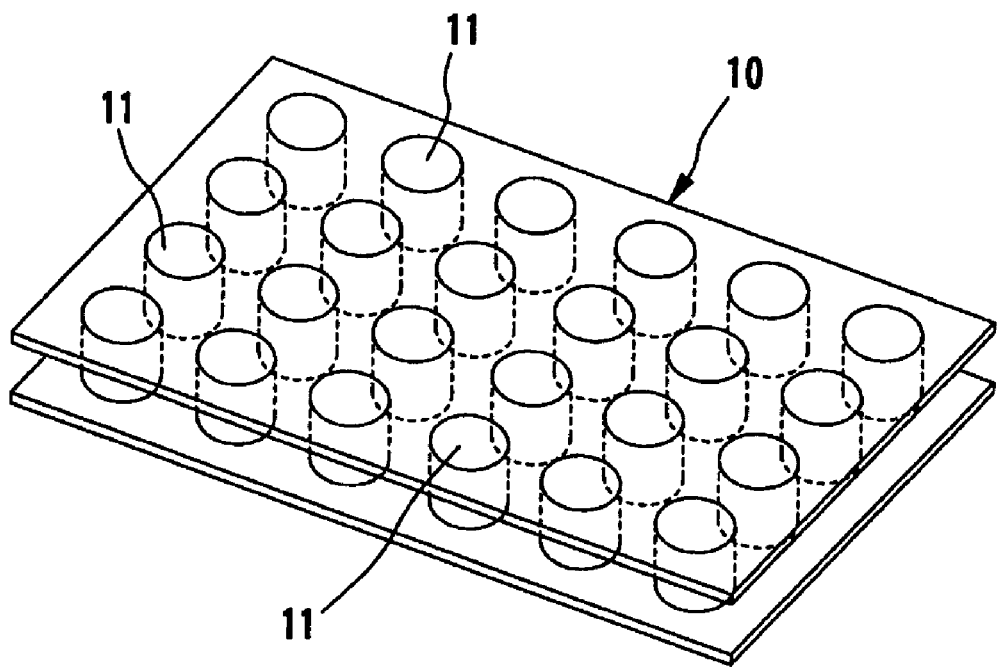
FIG. 3A is a perspective view showing a construction of a sample container.

Preferred embodiments according to the present invention when a protein crystal is set as an evaluating target (a specific macromolecule crystal) will be described with reference to the drawings.

(Whole Construction of Apparatus)

FIG. 1 is a plan view showing the whole construction of a specific macromolecule crystal evaluating apparatus according to an embodiment, and FIG. 2 is a front view.

As shown in FIG. 1, the specific macromolecule crystal evaluating apparatus is equipped with a sample container accommodating portion 100, a supply robot 200, a sample container identifying portion 300, a feeding unit 200 (feeding means), a sample detecting stage 500, an X-ray measuring stage 600 and a central processing unit 700 (control means).

The sample container accommodating portion 100 is constructed by partition shelves on which plural sample containers 10 can be arranged and accommodated, and the sample containers 10 in which protein crystals are stored are arranged and mounted in the sample container accommodating portion 100.

Figure 3B:
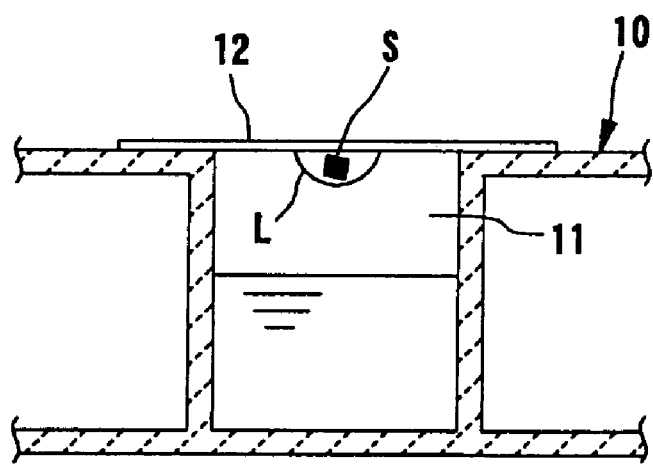
FIG. 3B is a partially enlarged front cross-sectional view.

It is preferable that a crystallization plate formed of material such as polyimide or the like through which ultraviolet light, visible light and X-ray are transmitted is used as the sample container 10. Many recess portions 11 are formed in the sample container 10 using the crystallization plate as shown in FIG. 3A, and a protein crystal S can be generated in each recess portion 11. Various methods containing a vapor diffusion method are known as a method of generating a protein crystal by using a crystallization plate. FIG. 3B is a schematic diagram showing the state that the protein crystal S is generated according to the vapor diffusion method, and the protein crystal S is generated in a drop of sample solution L placed on the lower surface of a cover plate 12. Protein crystals S can be separately generated in the many recess portions 11 formed in the sample container 10 while the generating condition is changed or the kind of the protein crystals S to be generated is changed.

The supply robot 200 is quipped with a robot arm that is freely expandable and contractable in the axial direction, freely movable in the height direction and swingable on the horizontal plane, and an opening/closing chuck 202 is provided to the tip of the robot arm 201. Each of the sample containers 10 accommodated in the sample container accommodating portion 100 is drawn out from the accommodating portion 100 while grasped by the opening/closing chuck 202, and it is first fed to a sample container identifying portion 300.

An information reading device for reading out identification information attached to each sample container 10 in advance is mounted in the sample container identifying portion 300, and the sample container 10 is disposed at a position (information reading position) at which the information reading device can read the identification information. Here, when a bard code is used as the identification information, the information reading device is constructed by a bar code reader.

In this embodiment, a container re-grasping portion 310 is provided in the neighborhood of the sample container accommodating portion 100 for the purpose of surely grasping and feeding the sample container 10 drawn out from the sample container accommodating portion 100 by the opening/closing chuck 202. A sample container 10 drawn out from the sample container accommodating portion 100 is temporarily put on the container re-grasping portion 310. Then, it is accurately grasped by the opening/closing chuck 202 again and fed to the sample container identifying portion 300.

The feeding unit 400 comprises a sample table 401 on which the sample container 10 is put, an XYZ table 402 for mounting the sample table 401, and a slider 403 for feeding the XYZ table 402 integrally with the sample table 401.

Figure 4A:
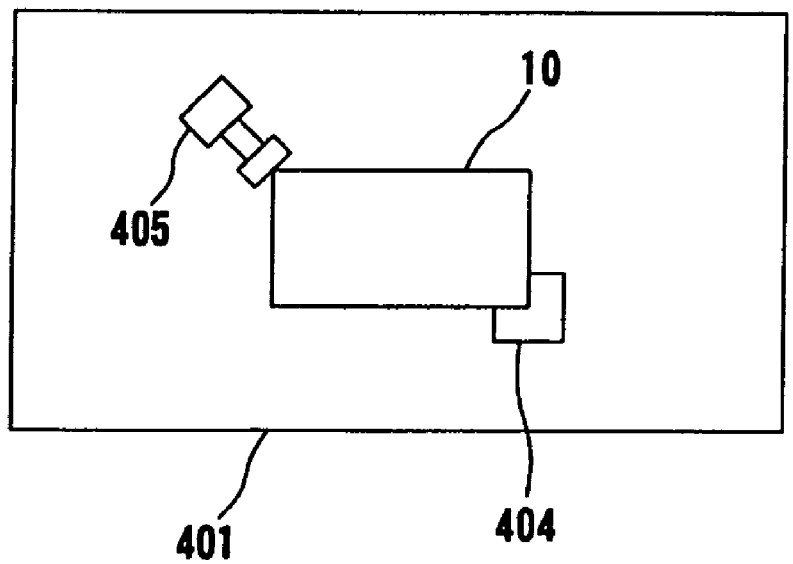
FIG. 4A is a plan view showing the construction of a sample table.

As shown in FIG. 4A, the sample table 401 is provided with a positioning block 404 and a pressing actuator 405 on the upper surface thereof, and a corner portion of the sample container 10 mounted on the upper surface is pressed by the actuator 405 so that another corner portion of the sample container 10 which is disposed diagonally to the corner portion concerned is brought into contact with the positioning block 404, whereby the sample container 10 is mounted at a fixed position on the sample table 401 at all times.

Figure 4B:
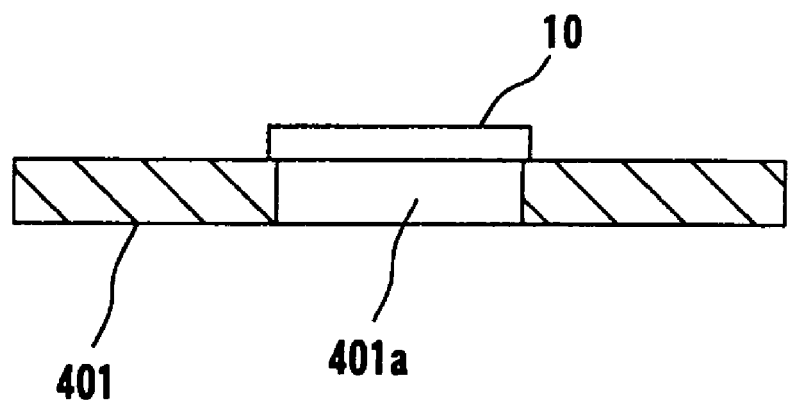
FIG. 4B is a front cross-sectional view showing the construction of the sample table.

As shown in FIG. 4B, the sample table 401 is provided with a through hole 401a is formed at the site at which the sample container 10 is put. The through hole 401a transmits therethrough ultraviolet light and visible light irradiated to the sample container 10 in a sample detecting stage 500 described later and X-ray irradiated to the protein sample S in the sample container in the X-ray measuring stage 600.

The XYZ table 402 is a mechanism for moving the sample table 401 in the X direction and Y direction orthogonal to each other on the horizontal plane and move the sample table 401 in the height direction (Z direction). The XYZ table 402 is mounted on the slider 403.

The slider 403 forms a feeding passage through which the sample detecting stage 500 and the X-ray measuring stage 600 are connected to each other, and has a function of linearly feeding the sample table 401 mounted on the XYZ table 402 between the sample detecting stage 500 and the X-ray measuring stage 600.

The sample detecting stage 500 is a stage for detecting the protein crystal S in the sample container 10 and recognizing the position of the center of gravity thereof. The X-ray measuring stage 600 is a stage for carrying out X-ray diffraction measurement on the protein crystal S in the sample container 10 detected by the sample detecting stage 500. Each stage will be described in detail later.

The central processing unit 700 is constructed by a general-purpose computer, and controls the driving of each part of the apparatus described above. The central processing unit 700 executes the identification of the protein crystal S and the recognition of the position of the center of gravity of the protein crystals in the sample detecting stage 500, and also executes the X-ray measurement processing in the X-ray measuring stage 600. Particularly, the central processing unit 700 has a function of controlling the XYZ table 402 and the slider 403 on the basis of the position information (the information of the position of the center of gravity) of the protein crystal S which is recognized on the basis of the information achieved in the sample detecting stage 500, and positioning the protein crystal S to the sample disposing portion 610 of the X-ray measuring stage 600.

Here, the driving of the slider 403 is controlled so that the slider 403 is gradually accelerated from the start time for a fixed period, then driven at a fixed speed and then gradually decelerated to be stopped at the sample disposing portion 610. Accordingly, the inertial force is suppressed and the protein crystal S in the sample container 10 mounted on the sample table 401 can be prevented from moving.

[Sample Detecting Stage]

Next, the sample detecting stage 500 will be further described in detail.

Figure 5:
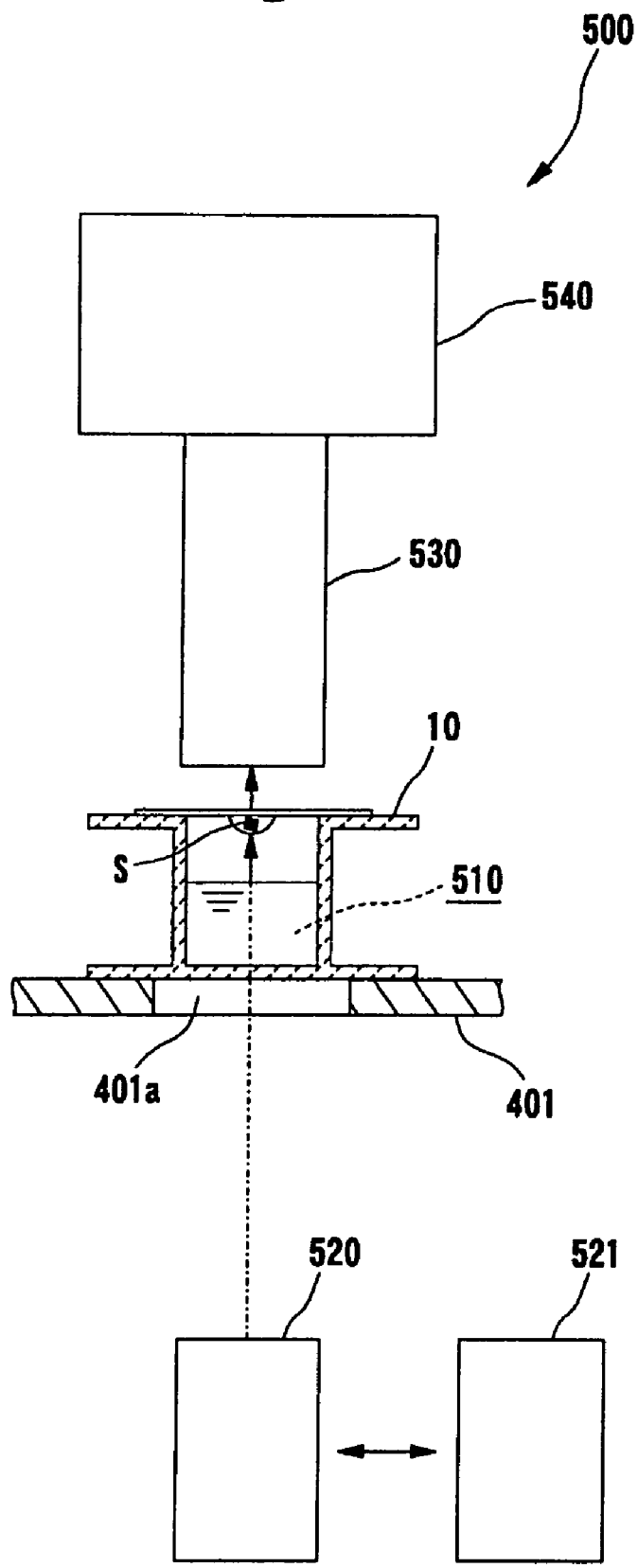
FIG. 5 is a diagram showing the scheme of a sample detecting stage.

FIG. 5 is a diagram showing the outline of the sample detecting stage.

The sample detecting stage 500 is provided with a visible light irradiating unit 520 and an ultraviolet light irradiating unit 521 which are disposed at the lower side of a sample detector 510 in which the sample container 10 is disposed. The visible light irradiating unit 520 and the ultraviolet light unit 521 serve as light sources for irradiating visible light or ultraviolet light to the sample container 10 disposed in the sample detector 510.

The visible light irradiating unit 520 and the ultraviolet light irradiating unit 521 are laterally slid, and any one unit of them is disposed so as to confront the sample container 10. If a reflection mirror is disposed at the middle position between the sample container 10 and the visible light irradiating unit 520 and the ultraviolet light irradiating unit 521 to lead the visible light emitted from the visible light irradiating unit 520 or the ultraviolet light emitted from the ultraviolet light irradiating unit 521 to the sample container 10, it would be unnecessary that each irradiating unit 520, 521 is disposed so as to confront the sample container 10.

The sample container 10 is put on the sample table 401 as described above, and the sample detector 510 is disposed by the movement of the XYZ table 402 and the slider 403.

A microscope 530 and a two-dimensional image pickup unit 540 are disposed above the sample detector 510. The microscope 530 enlarges an image achieved when ultraviolet light or visible light is irradiated to the sample container 10 and transmitted therethrough, and leads the enlarged image to the two-dimensional image pickup unit 540. The microscope 530 is constructed so that the protein crystal S in the sample container 10 can be searched by varying the focal position thereof in the vertical direction.

CCD may be used as the two-dimensional image pickup unit 540. The two-dimensional image pickup unit 540 converts the enlarged image incident through the microscope 530 to an electrical signal (image data), and outputs the electrical signal to the central processing unit 700. The central processing unit 700 processes the image data input from the two-dimensional image pickup unit 540 to detect the protein crystal S in the sample container 10 and recognize the position thereof.

Figure 6:
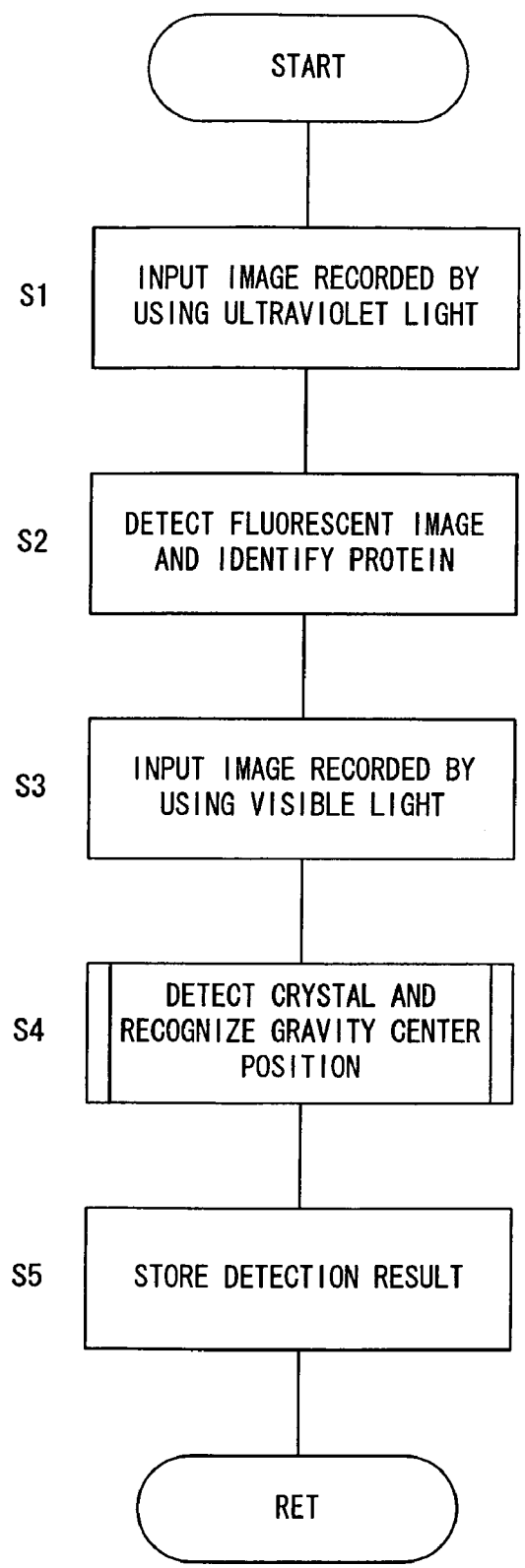
FIG. 6 is a flowchart showing a protein crystal detecting method executed by a central processing unit.
Figure 7:
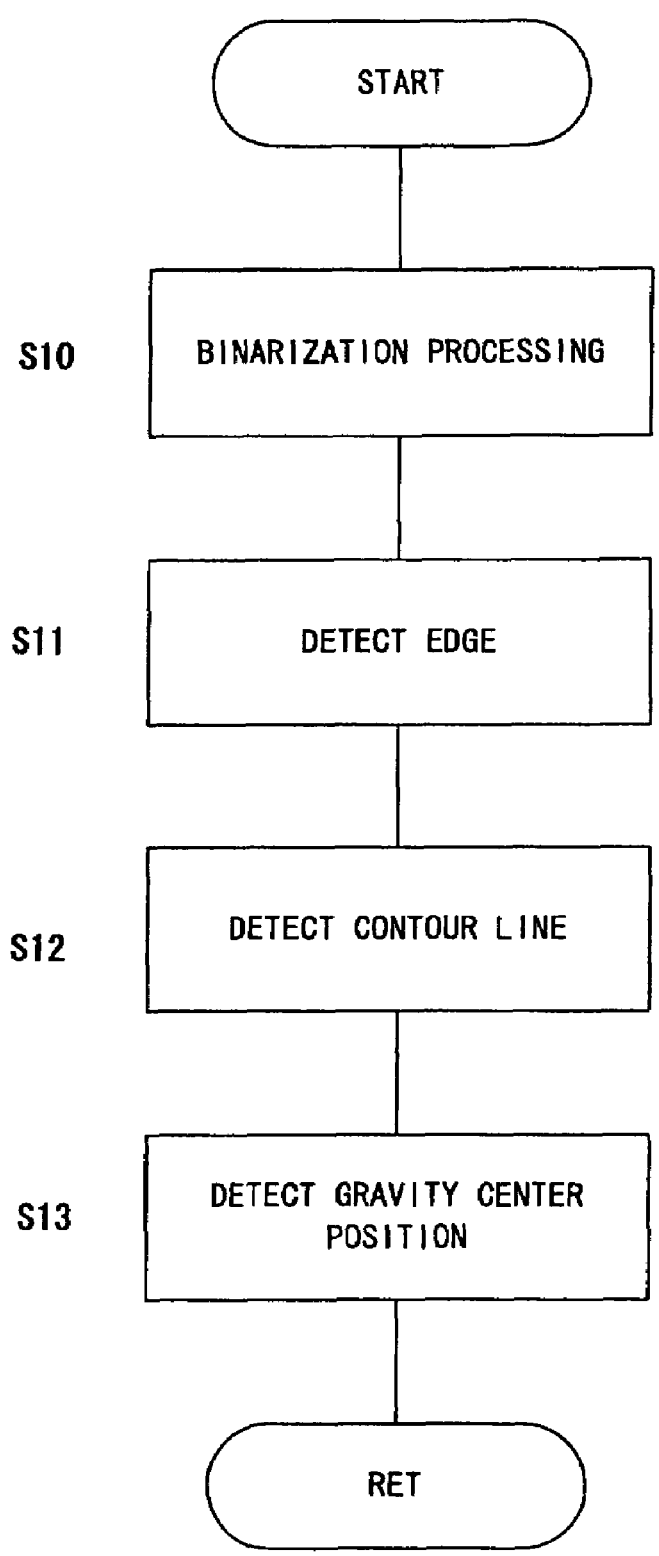
FIG. 7 is a flowchart showing a subroutine applied to step S4 of FIG. 6.

FIGS. 6 and 7 are flowcharts showing the method of detecting the protein crystal that is executed by the central processing unit.

First, the light source is set to the ultraviolet light irradiating unit 521, and the ultraviolet light emitted from the ultraviolet light irradiating unit 521 is irradiated to the sample container 10.

The image achieved when the ultraviolet light is transmitted through the sample container 10 is enlarged by the microscope 530, and incident to the two-dimensional image pickup unit 540. The central processing unit 700 receives the image data transmitted from the two-dimensional image pickup unit (step S1), and detects a fluorescent image from the image data (step S2). That is, since the protein crystal S generated in the sample solution L generates fluorescence when ultraviolet light is irradiated to the protein crystal S, the fluorescent image is incident to the two-dimensional image pickup unit 540. Therefore, the central processing unit 700 analyzes the image data input from the two-dimensional image pickup unit 540 to detect the fluorescent image, and grasps the position of the fluorescent image, that is, the protein.

The position of the protein thus grasped is the position on the horizontal plane (xy coordinate), and the position in the height direction (z coordinate) is grasped on the basis of the focal position of the microscope 530.

Subsequently, the light source is switched from the ultraviolet irradiation unit 521 to the visible light irradiating unit 520, and the visible light emitted from the visible light irradiating unit 520 is irradiated to the sample container 10. At this time, the visible image achieved when the visible image is transmitted through the sample container 10 is enlarged by the microscope 530, and incident to the two-dimensional image pickup unit 540. The central processing unit 700 receives the image data transmitted from the two-dimensional image pickup unit 540 (step S3), and processes the image data to detect the crystal in the sample solution L and also recognize the position of the center of gravity (step S4).

The step S4 (crystal detecting step) is processed along the subroutine shown in FIG. 7. That is, the image data input from the two-dimensional image unit 540 is binarized by using a predetermined threshold value as a reference, and each pixel on the xy coordinate is converted to binary data of "1" or "0" (step S10).

Figure 8:
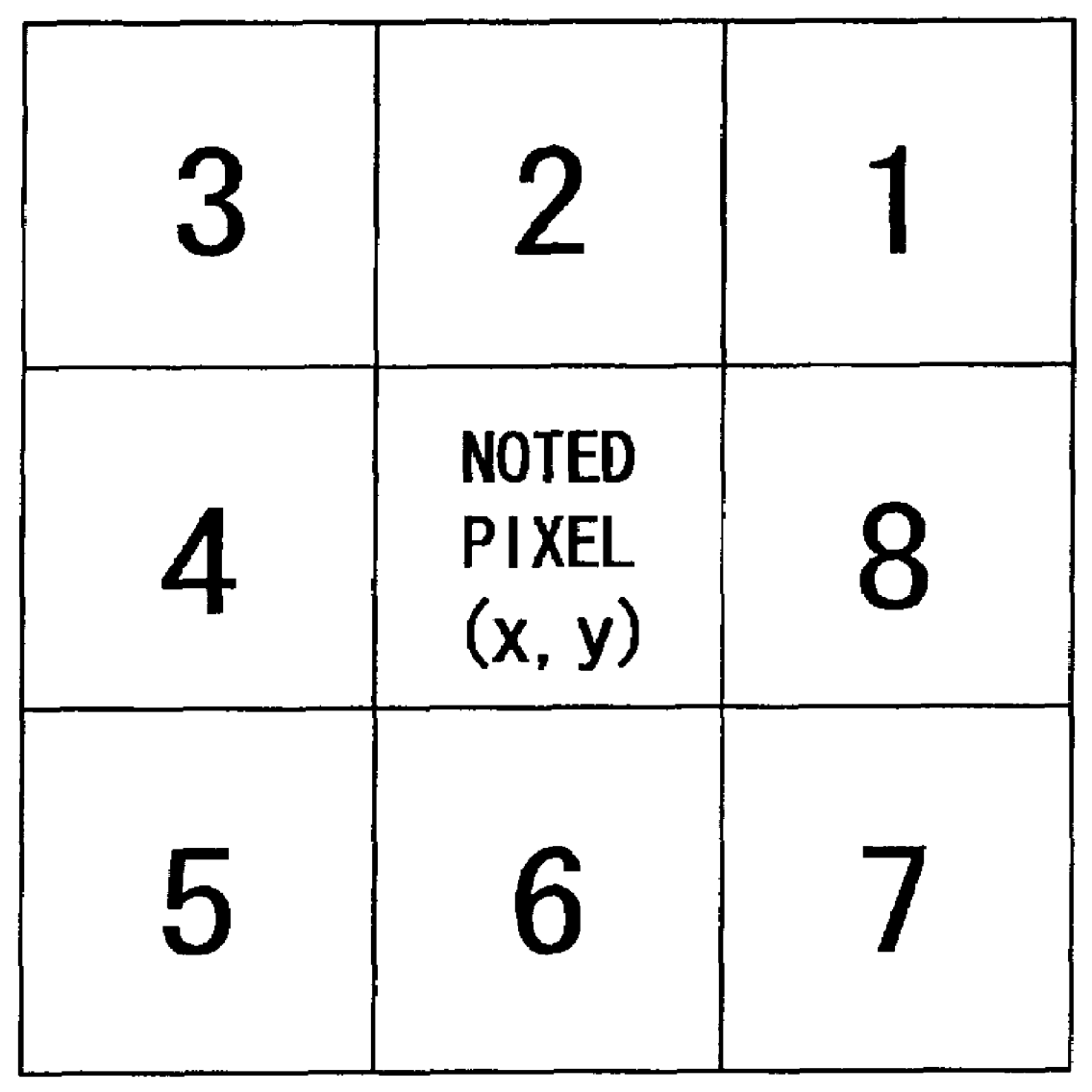

Subsequently, the pixels corresponding to the edge of the sample existing in the sample solution L are detected on the basis of the binarized image data (step S11). Here, it is judged whether a noted pixel as an identification target is black (data "1") or not as shown in FIG. 8. If the noted pixel is black, it is likewise judged whether each of the surrounding pixels (pixels 1 to 8) around the noted pixel concerned is black (data "1") or white "data "0").

If all the surrounding pixels (pixels 1 to 8) are white (data "0"), it is concluded that the noted pixel concerned is an isolated point. On the other hand, if all the surrounding pixels (pixels 1 to 8) are black (data "1"), it is concluded that the noted pixel concerned is an internal point of the image. As described above, all the pixels corresponding to isolated points and internal points are excluded, and a noted pixel for which some of the surrounding pixels (pixels 1 to 8) of the noted pixel concerned are white (data "0") is recognized as an edge of the sample, and the xy coordinate thereof is stored.

The above processing is executed on all the pixels of the xy coordinate system, and all the pixels corresponding to the edge of the sample are extracted.

Subsequently, the pixels corresponding to the edge of the extracted sample are noted, and the neighboring pixels are linked to one another to detect the contour line of the sample (step S12). If the start and end points of the contour line are coincident with each other, the contour line is judged as a closed contour line. Furthermore, the sample having the closed contour line is judged as a crystal having a fixed area. On the other hand, the sample whose contour line is not closed is excluded as a non-crystallized material such as aggregation or the like.

Subsequently, the internal area of the sample having the closed contour line (that is, crystal) is recognized, and the position of the center of gravity of the internal area is calculated by using a well-known calculation method (step S13).

As a method of calculating the position of the gravity center of a planar image, the moment quantity of a linked figure S recognized as a crystal is determined, and the position of the gravity center is calculated on the basis of the moment quantity. That is, when the weight of each pixel of the linked figure S is equally set to 1, the moment M(m,n) is defined by the following equations.

$$M(m, n) = \sum_{(x,y) \in S} (x^m \times y^n)$$

M(0, 0) represents the area of the linked figure S

M(1,0) represents the moment with respect to the x-axis

M(0,1) represents the moment with respect to the y-axis

The gravity center coordinate (p, q) can be calculated by using the above moment quantity according to the following equations:

$P = M(1,0)/M(0,0)$ $Q = M(0,1)/M(0,0)$

After the gravity center position of the crystal thus detected is calculated, the central processing unit 700 returns to the main routine shown in FIG. 6 again, and superposes the position of the protein detected on the basis of the fluorescent image with the position of the crystal detected on the basis of the visible light image to recognize the protein crystal S. The gravity center position achieved n step S13 of FIG. 7 for the protein crystal S is stored (step S5). As described above, the gravity center position of the protein crystal S existing in the sample container 10 can be automatically detected.

Figure 9A:
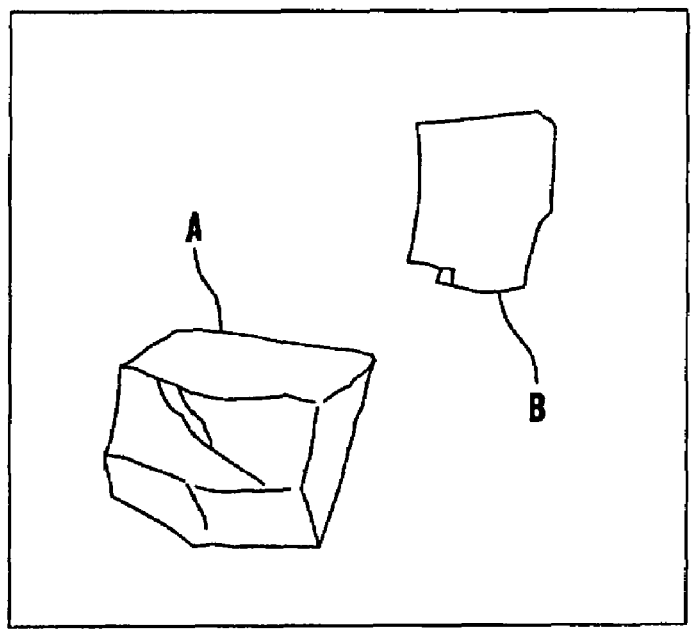
FIGS. 9A and 9B are sketches showing microscopic observation images achieved by observing sample solution containing the mixture of a protein crystal and a crystal of material generating no self-fluorescence.
Figure 9B:
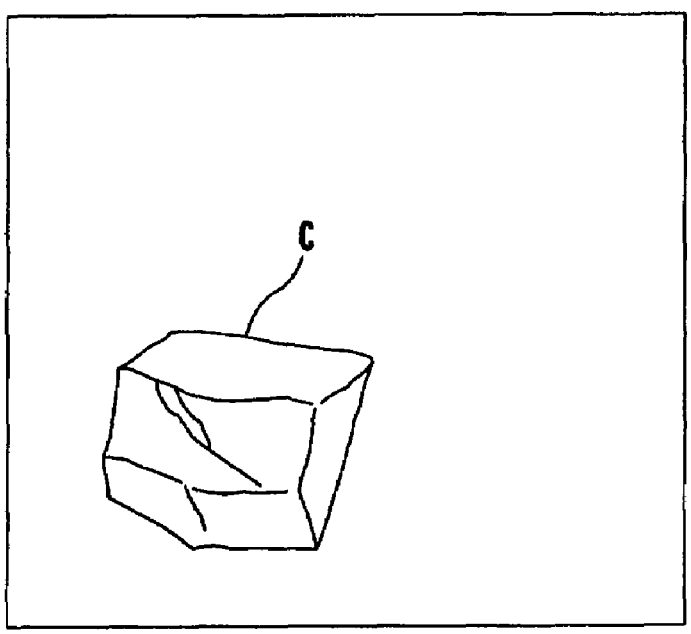

FIGS. 9A and 9B are sketches showing microscope images achieved by observing sample solution containing the mixture of a protein crystal and a crystal of a material generating no self-fluorescence, wherein FIG. 9A shows a visible light image achieved by irradiating visible light to the sample solution, and FIG. 9B shows a fluorescent light image achieved by irradiating ultraviolet light to the sample solution.

As shown in FIG. 9A, when visible light is irradiated to the sample solution, a visible light image A of the protein crystal and a visible light image B of the other crystal B are observed. In this image, it is unidentifiable which one of the visible images corresponds to the protein crystal.

However, as shown in FIG. 9B, when ultraviolet light is irradiated to the sample solution, only a fluorescent image C of the protein crystal is observed, and the other crystal is not detected. Accordingly, by superposing the visible light image A with the fluorescent image C, the position of the protein crystal can be recognized.

Figure 10A:
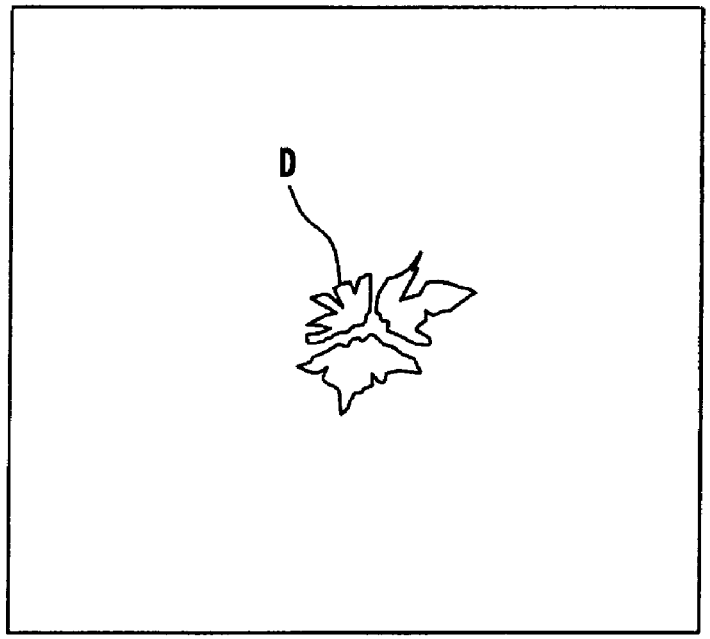
FIGS. 10A and 10B are sketches showing microscopic observation images achieved by observing sample solution containing aggregation of protein.
Figure 10B:
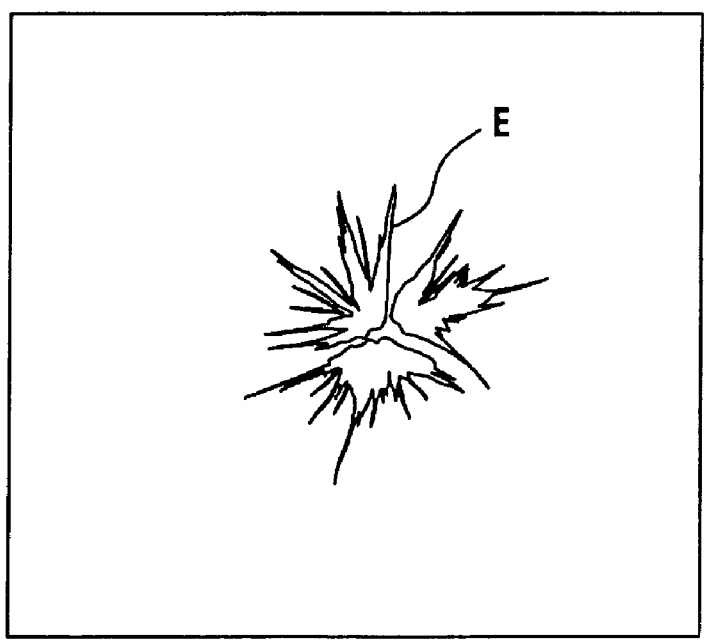

FIGS. 10A and 10B are sketches of microscope images achieved by observing the sample solution containing aggregation of protein, wherein FIG. 10A shows a fluorescent image achieved by irradiating ultraviolet light to the sample solution, and FIG. 10B shows a visible image achieved by irradiating visible light to the sample solution.

As shown in FIG. 10A, when the ultraviolet light is irradiated to the sample solution, a fluorescent image D emitted from the aggregation of the protein is observed. It is unidentifiable on the basis of the fluorescent image D which one of the aggregation of the protein and the crystal of the protein it corresponds to.

However, as shown in FIG. 10B, when the visible light is irradiated to the sample solution, a visible light image having a needle-like shape characteristic of the aggregation of protein is observed, and thus the observation target can be identified as the aggregation of the protein.

As described above, the position of the protein crystal can be recognized with excluding the crystals of materials other than the protein and the aggregation of the protein by integrating the fluorescent image achieved when the ultraviolet light is irradiated to the sample solution and the visible light image achieved when the visible light is irradiated to the sample solution.

[X-Ray Measuring Stage]

Next, the X-ray measuring stage will be further described in detail.

Figure 11:
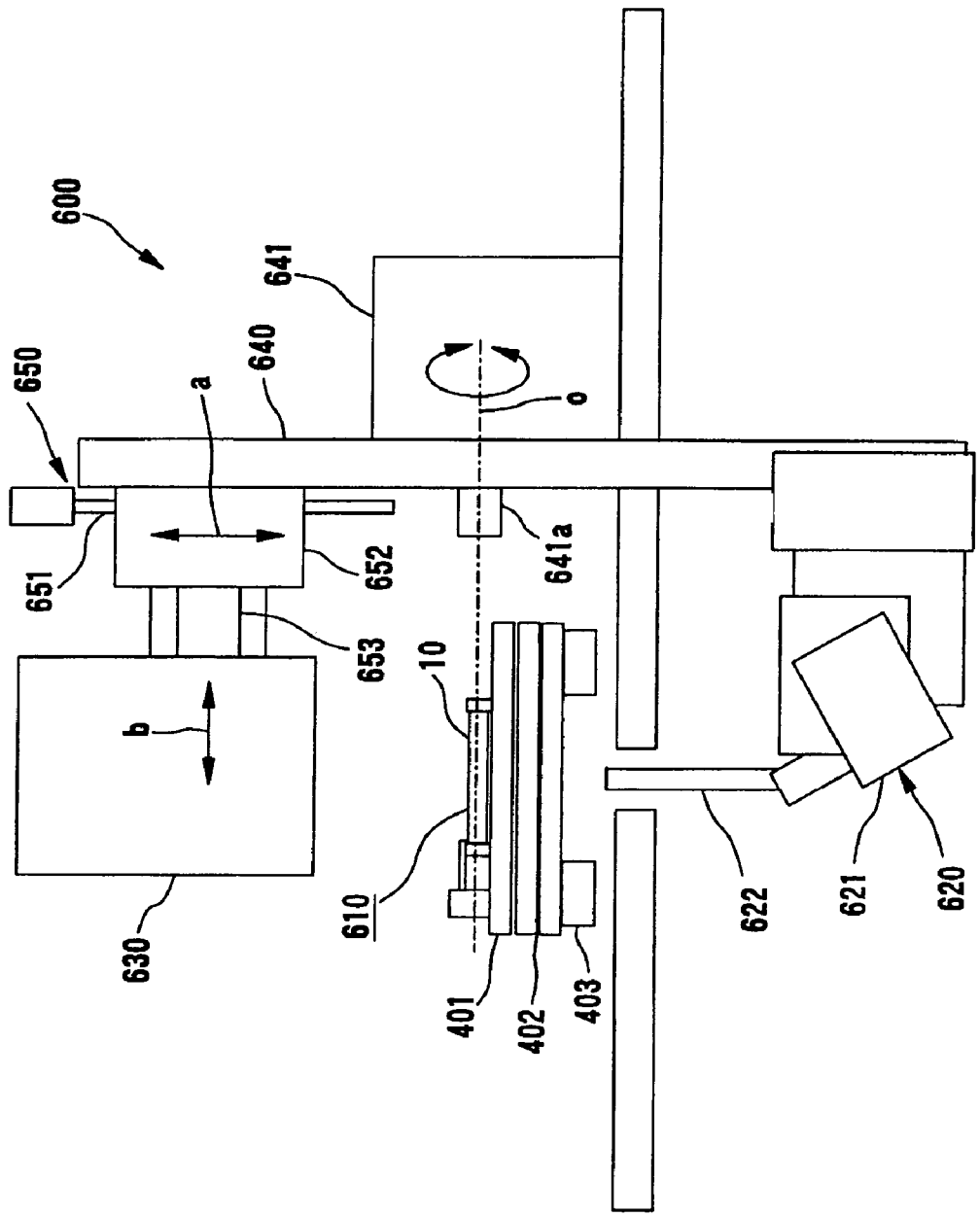
FIG. 11 is a side view showing the construction of an X-ray measuring stage.
Figure 12:
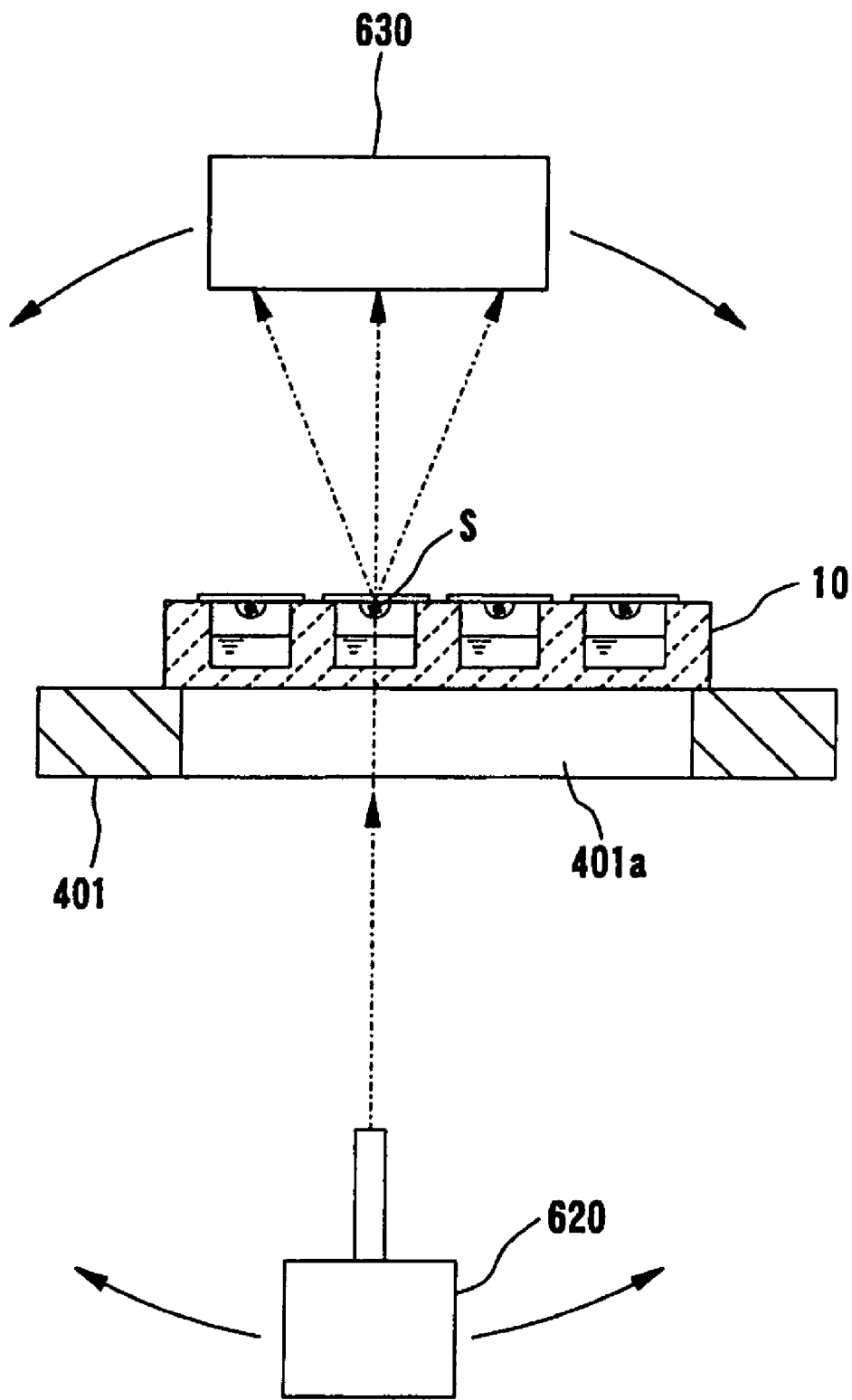
FIG. 12 is a diagram showing the principle of measuring a protein crystal in the X-ray measuring stage.

FIG. 11 is a side view showing the construction of the X-ray measuring stage, and FIG. 12 is a diagram showing the principle of measuring the protein crystal in the X-ray measuring stage.

As shown in FIG. 11, the X-ray measuring stage 600 is provided with an X-ray irradiating unit 620 (X-ray irradiating means) and an X-ray detector 630 (X-ray detecting means) disposed at the lower and upper sides of the sample disposing portion 610, respectively.

As described above, the sample container 10 put on the sample table 401 is positioned to and disposed at the sample disposing portion by moving the XYZ table 402 and the slider 403.

The X-ray irradiating unit 620 contains an X-ray source 621 and an X-ray optical system 622. An X-ray generator for a laboratory which contains an electron gun and a target is used as the X-ray source 621. This type of X-ray generator is remarkably smaller in dimension and weight as compared with large-scale X-ray generating equipment for generating radiation light. Therefore, it can be mounted on a rotary arm and rotatably driven as described later.

The X-ray optical system 622 has a function of selecting only X-ray having a specific wavelength (made monochromatic), and converging the X-ray to the sample disposing portion 610, and it is constructed by combining optical devices such as a confocal mirror, a collimator, etc.

A two-dimensional X-ray detector is used as the X-ray detector 630. Particularly, in this embodiment, CCD is used as the X-ray detector 630. Therefore, the intensity of the diffracted X-ray detected on the plane is converted to an electrical signal, and the electrical signal is output to the central processing unit 700.

The X-ray irradiating unit 620 and the X-ray detector 630 are mounted on the rotary arm 640. The rotary arm 640 is designed in any shape, and for example it may be designed in a plate-like shape or rod-like shape. The X-ray irradiating unit 620 is mounted at one end portion of the rotary arm 640, and the X-ray detector 630 is mounted at the other end portion so as to confront the X-ray irradiating unit 620.

The center portion of the rotary arm 640 is mounted to the rotating shaft 641a of the rotationally driving mechanism 641, and the rotary arm 640 is rotatable around the rotating shaft 641a by any angle by the rotationally driving mechanism 641. The center line O of the rotating shaft 641a of the rotationally driving mechanism 641a is located substantially horizontally, and the optical axis of the X-ray radiated from the X-ray irradiating unit 620 is adjusted so as to cross the center line O of the rotating shaft 641a. This rotationally driving mechanism 641 comprises a driving motor such as a stepping motor or the like which can control the rotational angle with high precision, and a gear mechanism for transferring the rotation of the driving motor to the rotating shaft 641a, and the rotational angle of the driving motor is controlled by the central processing unit 700. It is preferable that the rotational angle is freely controllable in the range of about 45° in both the forward and reverse directions.

In this embodiment, the X-ray irradiating unit 620 mounted on the rotary arm 640 is disposed below the sample disposing portion 610, and the X-ray detector 630 is disposed above the sample disposing portion 610. X-ray is irradiated from the lower side to the protein crystal S generated in the sample container 10 on the sample disposing portion 610, and diffracted X-ray reflected from the protein crystal S is detected by the X-ray detector 630 above the sample container 10. The arrangement of the X-ray irradiating unit 620 and the X-ray detector 630 may be inverted in the vertical direction so that the X-ray irradiating unit 620 is disposed above the sample disposing portion 610 and the X-ray detector 630 is disposed below the sample disposing portion 610.

Furthermore, a detection position adjusting mechanism 650 is affixed to the X-ray detector 630. The detection position adjusting mechanism 650 is a mechanism for moving the X-ray detector 630 in the radial direction (the direction a of the figure) and in a direction (the direction of b in the figure) parallel to the sample container 10 disposed on the sample disposing portion 610. In the construction shown in FIG. 11, the detection position adjusting mechanism 650 comprises a first guide rail 651 disposed on the rotary arm 640, a first moving table 652 movable along the first guide rail 651, a second guide rail 653 extending from the moving table 652 in the direction of b, a second moving table (not shown) movable along the second guide rail 653, and a driving motor (not shown) for driving each moving table, and the X-ray detector 630 is fixed to the second moving table.

Next, the method of measuring the protein crystal in the X-ray measuring stage 600 will be described.

The protein crystal S in the sample container is automatically positioned to the sample disposing portion 610 by moving the XYZ table 402 and the slider 403.

Here, the distance between the protein crystal S and the X-ray detector 630 is adjusted as occasion demands. That is, as the X-detector 630 approaches to the protein crystal S, the diffraction spots of the X-ray reflected radially from the protein crystal S can be detected in a broad angle range. However, when the reciprocal lattice density of the protein crystal S is high, if the X-ray detector 630 approaches to the protein crystal S, there is a risk that the diffraction spots of the X-ray reflected radially from the protein crystal S are detected with being overlapped with one another. Therefore, by adjusting the movement of the X-ray detector 630 in the direction of a of FIG. 11 through the detection position adjusting mechanism 650, the distance between the protein crystal S and the X-ray detector 630 can be properly adjusted, and suitable detection data can be achieved.

Furthermore, by adjusting the movement of the X-ray detector 630 in the direction of b of FIG. 11 through the detection position adjusting mechanism 650, the detection range of the diffracted X-ray reflected radially from the protein crystal S can be varied.

Subsequently, X-ray is irradiated from the X-ray irradiating unit 620 to execute the X-ray diffraction measurement. As shown in FIG. 12, the X-ray irradiated from the X-ray irradiating unit 620 is incident from the lower side to the protein crystal S in the sample container 10. The X-ray is radially diffracted from the protein crystal S, and the diffracted X-ray is detected by the X-ray detector 630. The central processing unit 700 executes the crystal evaluation and the crystal structure analysis on the basis of the intensity data of the diffracted X-ray thus detected.

Furthermore, when X-ray is irradiated from various angles to the protein crystal S to detect the intensity of the diffracted X-ray, the rotary arm 640 is rotated by the rotationally driving mechanism 641 to adjust the angles of the X-ray irradiating unit 620 and the X-ray detector 630 to the lattice plane of the protein crystal S, and the X-ray diffraction measurement described above is repeated. By this operation, the integrated intensity of the diffracted X-ray from the protein crystal S can be determined without rotating the sample container 10, and the crystal structure analysis having high reliability can be implemented on the basis of the integrated intensity thus determined.

The above embodiments have been described by setting the protein crystal as a detection target. However, the target of the method of the present invention is not limited to the protein crystal, and various kinds of specific macromolecule crystals each having the characteristic that they generate fluorescence when ultraviolet light is irradiated to them may be used as detection targets.

As described above, according to the present invention, the specific macromolecule crystal in the sample contained is detected in the sample detecting stage, and the feeding means is controlled on the basis of the information achieved there, whereby the specific macromolecule crystal is positioned to the sample disposing portion of the X-ray measuring stage. Therefore, the work form the detection of the specific macromolecule crystal to the positioning to the sample disposing portion can be automated, and thus the evaluation processing can be speeded up.

The invention claimed is:

1. An apparatus for evaluating a specific macromolecule crystal in a sample contained in a sample container through which X-rays, ultraviolet light and visible light are transmissible, comprising:
   a sample detecting device for detecting the specific macromolecule crystal in the sample container;
   an X-ray measuring device that is disposed so as to be spaced from the sample detecting device and carries out an X-ray diffraction measurement of the specific macromolecule crystal;
   feeding means for feeding the sample container from the sample detecting device to the X-ray measuring device; and
   control means for identifying the position of the specific macromolecule crystal on the basis of information generated in the sample detecting device and controlling the feeding means on the basis of the position of the specific macromolecule crystal to position the specific macromolecule crystal on a sample disposing portion of the X-ray measuring device, wherein
   the sample detecting device comprises specific macromolecule detecting means for irradiating ultraviolet light on the sample container and detecting a fluorescent image emitted from the sample in the sample container; and
   the control means is configured to identify a specific macromolecule based on said fluorescent image detected by the specific macromolecule detecting means.

2. The apparatus according to claim 1, wherein the sample detecting device comprises:
   a crystal detecting means for detecting the outline of a crystal in the sample from a visible light image of the sample contained in the sample container, wherein the control means is configured to identify the specific macromolecule crystal based on said fluorescent image detected by the specific macromolecule detecting means and based on said outline of said crystal detected by the crystal detecting means, and said control means is configured to determine the position of the specific macromolecule crystal.

3. The apparatus according to claim 1, wherein the X-ray measuring device comprises:
   X-ray irradiating means for irradiating X-rays from the upper side or lower side to the specific macromolecule crystal in the sample container disposed on the sample disposing portion;
   X-ray detecting means disposed so as to face the X-ray irradiating means through the sample container, said X-ray detecting means being configured to detect diffracted X-rays from the specific macromolecule crystal transmitted through the sample container;
   a rotary arm for supporting the X-ray irradiating means and the X-ray detecting means; and
   a rotationally driving mechanism for rotating the rotary arm with respect to a shaft center by any angle.

4. The apparatus according to claim 1, wherein the feeding means comprises a sample table on which a sample container is mounted, an XYZ table for mounting the sample table thereon and moving the sample table in X and Y directions orthogonal to each other along a plane and in a height direction perpendicular to said plane, and a slider for feeding the XYZ table from the sample detecting device to the X-ray measuring device.

5. An apparatus for evaluating a specific macromolecule crystal in a sample contained in a sample container through which X-rays, ultraviolet light and visible light are transmissible, comprising:

a sample detecting device for detecting the specific macromolecule crystal in the sample container;

an X-ray measuring device that is disposed so as to be spaced from the sample detecting device and carries out an X-ray diffraction measurement of the specific macromolecule crystal;

feeding means for feeding the sample container from the sample detecting device to the X-ray measuring device; and control means for identifying the position of the specific macromolecule crystal on the basis of information generated in the sample detecting device and controlling the feeding means on the basis of the position of the specific macromolecule crystal to position the specific macromolecule crystal on a sample disposing portion of the X-ray measuring device, wherein the sample detecting device comprises specific macromolecule crystal detecting means for irradiating ultraviolet light on the sample container and detecting a fluorescent image emitted from the sample in the sample container and for irradiating visible light on the sample container and detecting the outline of a crystal in the sample from a visible light image of the sample contained in the sample container; and the control means is configured to identify the specific macromolecule crystal and to determine the position of the specific macromolecule crystal based on said fluorescent image detected by the specific macromolecule crystal detecting means and based on said outline of said crystal detected by the specific macromolecule crystal detecting means.

6. The apparatus according to claim 5, wherein the X-ray measuring device comprises:

X-ray irradiating means for irradiating X-rays from the upper side or lower side to the specific macromolecule crystal in the sample container disposed on the sample disposing portion;

X-ray detecting means disposed so as to face the X-ray irradiating means through the sample container, said X-ray detecting means being configured to detect diffracted X-rays from the specific macromolecule crystal transmitted through the sample container;

a rotary arm for supporting the X-ray irradiating means and the X-ray detecting means; and a rotationally driving mechanism for rotating the rotary arm with respect to a shaft center by any angle.

7. The apparatus according to claim 5, wherein the feeding means comprises a sample table on which a sample container is mounted, an XYZ table for mounting the sample table thereon and moving the sample table in X and Y directions orthogonal to each other along a plane and in a height direction perpendicular to said plane, and a slider for feeding the XYZ table from the sample dgetecting device to the X-ray measuring device.

* * * * *